United States Patent [19]
Gerber et al.

[11] Patent Number: 5,442,446
[45] Date of Patent: Aug. 15, 1995

[54] INSPECTION OF TRANSPARENT CONTAINERS

[75] Inventors: Stephen M. Gerber, Petersburg, Mich.; James A. Ringlien, Maumee, Ohio

[73] Assignee: Owens-Brockaway Glass Container Inc., Toledo, Ohio

[21] Appl. No.: 292,704

[22] Filed: Aug. 19, 1994

[51] Int. Cl.⁶ ............................................. G01N 21/90
[52] U.S. Cl. .................................... 356/428; 356/240; 348/127
[58] Field of Search ................................ 356/240, 428; 250/223 B; 348/127, 131

[56] References Cited

U.S. PATENT DOCUMENTS

| | | |
|---|---|---|
| 3,601,616 | 8/1971 | Katsumata . |
| 3,927,923 | 12/1971 | Knapp ................................. 356/427 |
| 3,932,763 | 1/1976 | Weinstein . |
| 4,025,201 | 5/1977 | Deane ................................. 356/240 |
| 4,280,624 | 7/1981 | Ford ................................... 356/240 |
| 4,509,081 | 4/1985 | Peyton et al. ...................... 348/127 |
| 4,601,395 | 7/1986 | Juvinall et al. . |
| 4,620,090 | 10/1986 | Ducloux . |
| 4,625,107 | 11/1986 | Planke . |
| 4,843,231 | 6/1989 | Caloyannis et al. . |
| 4,868,404 | 9/1989 | Hajime . |
| 4,958,223 | 9/1990 | Juvinall et al. . |
| 5,136,157 | 8/1992 | Apter et al. . |
| 5,175,428 | 12/1992 | Agerskov et al. . |
| 5,233,186 | 8/1993 | Ringlien ........................... 356/240 |
| 5,256,871 | 10/1993 | Baldwin . |

Primary Examiner—Richard A. Rosenberger

[57] ABSTRACT

Apparatus for inspecting transparent containers having sidewall portions of differing optical properties that includes a pair of discrete light sources for directing light energy through the adjacent essentially discrete portions of the containers having the differing optical properties. A camera receives light energy directed through the container from both of the light sources as a single image of the entire portion of the container illuminated by both light sources. Commercial variations are detected as a function of variations in light intensity at the camera. The camera includes an array sensor that receives light energy transmitted through both of the container portions, and is scanned at increments of container rotation so as to develop an electronic image of the entire portion of the container illuminated by the light sources. The light sources are coordinated with the imaging electronics such that the electronic image has uniform optical properties in all portions of the image in the absence of commercial variations at the container.

10 Claims, 1 Drawing Sheet

INSPECTION OF TRANSPARENT CONTAINERS

The present invention is directed to inspection of transparent containers for commercial variations that affect optical properties of the containers, and more particularly to an apparatus and method for inspecting containers having sidewall portions of differing optical properties.

BACKGROUND AND OBJECTS OF THE INVENTION

In the manufacture of transparent containers such as glass bottles and jugs, various types of anomalies can occur in the sidewalls, heels, bottoms, shoulders and/or necks of the containers. These anomalies, termed "commercial variations" in the art, can affect commercial acceptability of the containers. The commercial variations may be opaque such as stones or metallic particles, or may be refractive such as blisters, bubbles or tears.

It has heretofore been proposed to employ electro-optical inspection techniques for detecting commercial variations that affect optical properties of the containers. The basic principle is that a light source is positioned to direct light energy onto the container, and a camera is positioned to receive an image of the portion of the container illuminated by the light source. The light source may be of uniform intensity, or may be configured to have an intensity that varies across one dimension of the light source. Opaque and refractive commercial variations in the portion of the container illuminated by the light source are detected as a function of light intensity in the image of the illuminated container received and stored at the camera. U.S. Pat. Nos. 4,601,395 and 4,958,223, both assigned to the assignee hereof, are illustrative of this technology.

U.S. Pat. No. 5,233,186, also assigned to the assignee hereof, discloses an apparatus and method for detecting commercial variations in transparent containers that include a conveyor for directing containers along a path through an inspection station, and a light source disposed on one side of the path for directing light energy through a container at the inspection station. A light sensing camera is positioned on the same side of the conveyor path, and a reflector is positioned on the opposing side of the conveyor path opposite the light source and camera for reflecting light energy transmitted from the light source through the container at the station back through the container to the camera. A beam splitter is positioned between the light source and the camera to separate the illumination light energy from the reflected light energy. The camera includes an array sensor that is scanned at increments of container rotation for developing a two-dimensional electronic image of the container. Commercial variations are detected as a function of variations in intensity of light energy received at the camera, and consequent variations in the two-dimensional electronic image of the container.

Although the systems disclosed in the noted patents address problems theretofore extant in the art, further improvements remain desirable. For example, the disclosed systems are not well adapted for inspecting portions of containers having differing optical properties, such as large jugs having knurled bands at the top and bottom of the jug sidewalls to help prevent scratching and cracking as the jugs hit each other during normal use. Because of the knurling, these bands exhibit a refractive characteristic—i.e., normal refractive noise—as compared with the remainder of the sidewall, and thus appear as dark bands in the image of the container independent of any commercial variations in the bands. It is therefore a general object of the present invention to provide an apparatus and method for electro-optically inspecting glass containers having portions, including particularly sidewall portions, of differing optical properties.

SUMMARY OF THE INVENTION

Apparatus for inspecting transparent containers having sidewall portions of differing optical properties in accordance with a presently preferred embodiment of the invention includes a pair of discrete light sources for directing light energy through adjacent essentially discrete portions of each container having the differing optical properties. A camera receives light energy directed through the container from both of the light sources as a single image of the entire portion of the container illuminated by both light sources. Commercial variations are detected as a function of variations in light intensity at the camera. The camera comprises an array sensor that receives light energy transmitted through both of the container portions, and is scanned at increments of container rotation so as to develop an electronic image of the entire portion of the container illuminated by the light sources. The light sources are coordinated with the imaging electronics such that the electronic image has uniform optical properties in all portions of the image in the absence of commercial variations at the container.

The light sources in the disclosed embodiment of the invention include a first light source positioned with the camera on one side of the container path through the inspection station, and a retroreflector disposed on the opposing side of the container path for receiving light energy from the first light source and reflecting the same back through the central portion of the container between knurled bands on the container sidewall. The second light source includes a pair of diffused light sources disposed above and below the retroreflector for illuminating the portions of the sidewall containing the knurled bands, with the light energy from the diffused light sources being transmitted through the knurled bands onto the camera. Either the camera scanning electronics or, more preferably the light sources, are adjusted during set-up so that the electronic image developed from both light sources of the entire container sidewall is of uniform intensity—i.e., without steps in brightness—in the absence of commercial variations in the container sidewall.

BRIEF DESCRIPTION OF THE DRAWING

The invention, together with additional objects, features and advantages thereof, will be best understood from the following description, the appended claims and the accompanying drawing in which:

DETAILED DESCRIPTION OF PREFERRED EMBODIMENT

Figure 1:
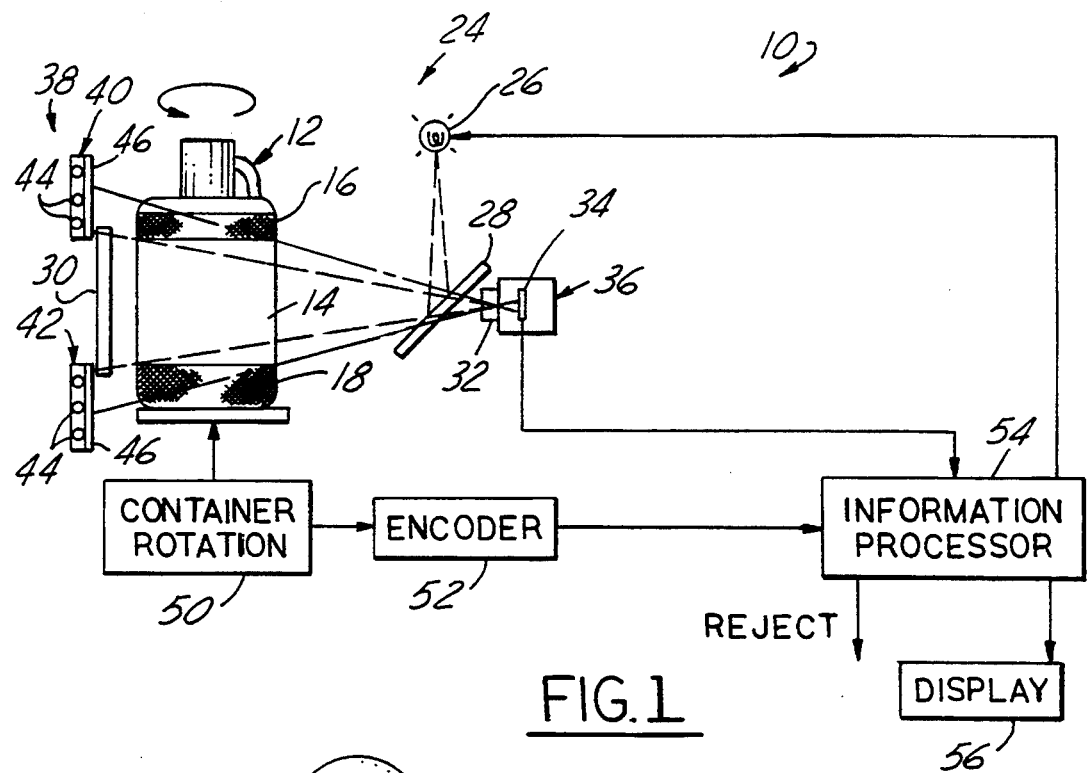
FIG. 1 is an electro-optical schematic diagram that illustrates a presently preferred embodiment of the invention.
Figure 2:
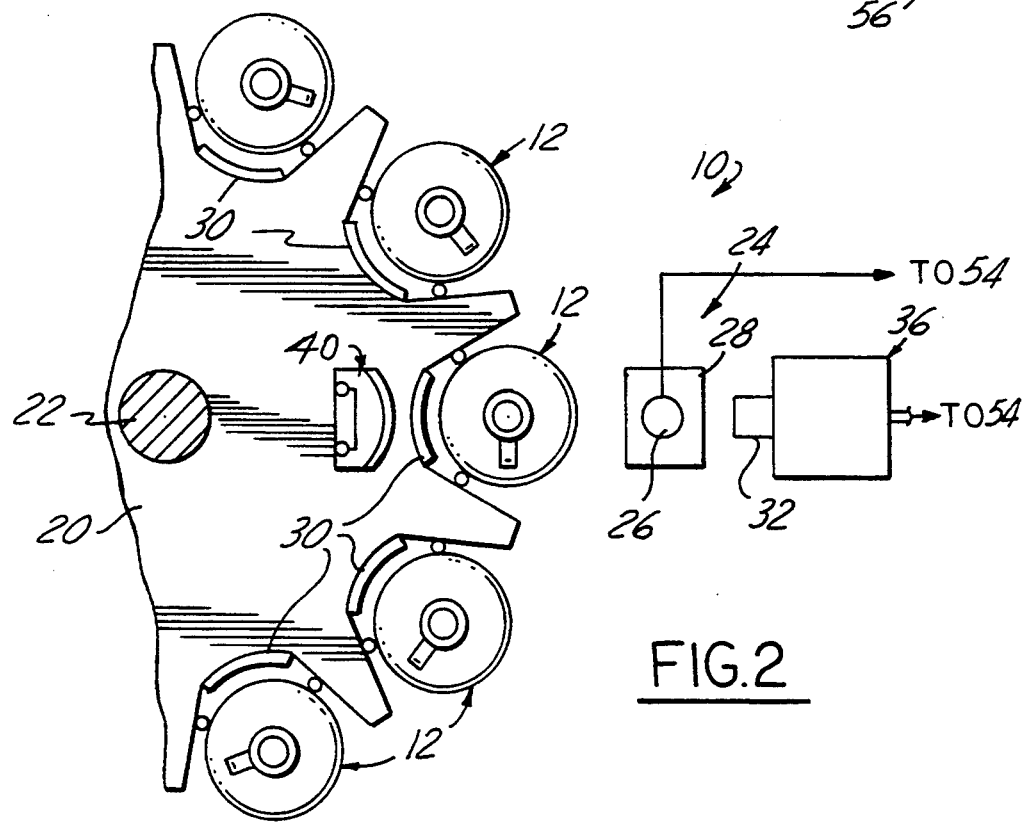
FIG. 2 is a fragmentary plan view of the container inspection station illustrated schematically in FIG. 1.

The drawing illustrates an apparatus 10 for inspecting transparent containers 12 for commercial variations that affect the optical properties of the containers. The particular containers 12 illustrated in the drawing comprise jugs having essentially transparent cylindrical sidewalls 14 with knurled bands 16,18 at the top and bottom edges of sidewall 14. These knurled bands 16,18 are conventionally provided to help prevent scratching and cracking of the jugs as they hit each other during normal handling.

Apparatus 10 includes a starwheel conveyor 20, such as that disclosed in above-noted U.S. Pat. No. 4,601,395, for conveying containers 12 along an arcuate path to and through an inspection station at which apparatus 10 is disposed. Sequential containers 12 are disposed in individual pockets of conveyor 20, which rotates about a central axis defined by a starwheel drive shaft 22. A first light source 24 in the form of one or more bulbs 26 is positioned to direct light energy onto a beam splitter 28, from which a portion of the light energy is reflected along an optical axis to and through the container 12 under inspection. A retroreflector 30 is disposed in each pocket of starwheel 20 to reflect the light energy incident thereon back through the container 12 under inspection along the same optical axis onto beam splitter 28. A portion of this reflected light energy is transmitted through beam splitter 28 to a lens system 32 having an entrance pupil disposed at the conjugate image of light source 24. Light energy is directed by system 32 onto an array sensor 34, which together with lens system 32 forms a light sensing camera 36.

A second light source 38 comprises a pair of fixed diffused light sources 40,42 respectively disposed above and below starwheel 20 at inspection station 10. Each diffused light source 40,42 includes one or more bulbs 44 that direct light energy onto container 12 at inspection station 10 through an associated diffuser 46. The diffused light energy from each light source 40,42 is directed through the adjacent knurled band 16,18 on container sidewall 14, and thence through beam splitter 28 onto array sensor 34 of camera 36. Thus, sensor 34 of camera 36 receives a composite or combined image of the central container sidewall portion 14 illuminated by light source 24 with retroreflector 30, and of container sidewall portions 16,18 illuminated by diffused light sources 40,42.

Container 12 at inspection station 10 is coupled to a suitable device 50, such as a motor and drive wheel, for rotating container 12 about its central axis while the container is held stationary by starwheel 20 during the inspection process. An encoder 52 is coupled to container rotating device 50 for providing a signal to an information processor 54 indicative of increments of container rotation, either directly as a function of angular increments of container rotation, or indirectly as a function of time increments during which container 12 is rotated at nominally constant angular velocity. Information processor 54 is coupled to camera 36 for scanning array sensor 34 at increments of container rotation, and thereby obtaining an electronic two-dimensional image of the entire container sidewall illuminated by retroreflective light source 24 and diffused light sources 40,42, as viewed through the remote wall of the container. Information processor 54 provides outputs to a suitable display 56, and to a suitable mechanism for rejecting a container 12 in which commercial variations exceed a desirable level.

In operation, containers 12 are fed to sequential pockets of starwheel conveyor 20, and are conveyed in turn to inspection station 10. At the inspection station, container 12 is held in stationary position and rotated about its central axis while central portion 14 of the container sidewall is illuminated by light source 24 and retroreflector 30, and the upper and lower knurled bands 16,18 are respectively illuminated by diffused light sources 40,42. It will be noted in FIG. 1 that retroreflectors 30 are dimensioned in cooperation with lamp 26 and the central portions 14 of containers 12 so that the entire back of container sidewall portion 14—i.e., the portion remote from camera 36—is illuminated by light source 24 and retroreflector 30. At the same time, the portions of the upper and lower knurled bands 16,18 at the back of the container are illuminated by diffused light sources 40,42. The image at camera 36 is thus a composite of the central container sidewall portion 14 illuminated by light source 24, and the upper and lower portions 16,18 illuminated by light sources 40,42. Preferably, the light sources are dimensioned for minimum overlap.

The system is adjusted during set-up to yield an electronic image of uniform intensity or brightness in the absence of commercial variations. Preferably, this is accomplished by adjusting intensity of the light sources so that the intensity seen by the camera through the knurled areas is the same as that seen through the center of the container. Alternatively, the adjustment may be made electronically by adjusting offset of individual pixels or pixel groups. Exemplary imaging techniques are disclosed, for example, in U.S. Pat. Nos. 4,701,612 and 4,958,223, both assigned to the assignee hereof.

There is thus developed in accordance with the present invention a composite two-dimensional electronic image of a container sidewall having portions of differing optical properties. That is, although containers 12 have a portion 14 that is essentially transparent and portions 16,18 that exhibit refractive characteristics, the electronic image developed by camera 36 and information processor 54 in accordance with the present invention is of uniform quality in which the differences in container sidewall optical properties have essentially been removed. In this way, detection of commercial variations in the container sidewall is greatly enhanced. In the preferred implementation of the invention, the light sources are of uniform intensity, so that the invention is particularly well adapted for detecting opaque and absorptive commercial variations, which yield dark spots or areas in an otherwise light background. The light sources may be configured to have intensities that vary across one dimension of the light sources, if desired, for detecting refractive commercial variations employing techniques disclosed in the patents noted above.

We claim:

1. Apparatus for inspecting transparent containers comprising:
    means for rotating a container about its axis,
    a pair of discrete light sources for directing light energy through adjacent essentially discrete portions of the container in said rotating means,
    means for receiving light energy directed through the container in said rotating means from both of said sources as a single image of the entire portion of the container illuminated by both of said sources, and
    means for detecting commercial variations in the container as a function of variations in light intensity at said sensing means.

2. The apparatus set forth in claim 1 wherein said means for detecting commercial variations in the container includes means for normalizing intensity of portions of said image corresponding to the essentially discrete portions of the container such that said image portions are of essentially the same image intensity in the absence of commercial variations in the container.

3. The apparatus set forth in claim 1 wherein said means for receiving light energy comprises an array sensor, and wherein said means for detecting commercial variations comprises means for scanning said array sensor to develop a two-dimensional image of the entire portion of the container illuminated by said light sources.

4. The apparatus set forth in claim 3 wherein said two-dimensional image consists of a two-dimensional array of image pixel signals, and means for selectively varying offset of said pixel signals such that portions of said two-dimensional image corresponding to the essentially discrete portions of the container are at essentially the same intensity level in the absence of commercial variations at the container.

5. The apparatus set forth in claim 1 wherein one of said light sources is disposed on the same side of the container as said light-receiving means, and reflector means is positioned on the opposite side of the container from said one light source and said light-receiving means for reflecting light energy from said one light source through the container onto said light-receiving means.

6. The apparatus set forth in claim 5 further including means for conveying containers along an arcuate path through an inspection station at which said pairs of light sources and said light-receiving means are disposed, said one light source and said light-receiving means being disposed outside of said path and said reflector means being disposed within said path.

7. The apparatus set forth in claim 6 wherein said conveying means comprises a starwheel conveyor having a circumferential array of pockets for receiving sequential containers, and wherein said reflector means comprises a plurality of retroreflectors disposed one in each of said pockets.

8. The apparatus set forth in claim 7 wherein the other light source comprises a diffused light source disposed within said arcuate path.

9. A method of inspecting sidewalls of transparent containers having sidewall portions of differing optical properties, said method comprising the steps of:
   (a) directing light energy through each said sidewall portion from an associated light source having properties coordinated with the differing optical properties of the sidewall portions so as to form a single image of the container sidewall having uniform optical properties, and
   (b) detecting commercial variations in the sidewall of the container as a function of variations in light energy in said image.

10. The method set forth in claim 9 wherein said step (b) comprises the steps of:
   (b1) forming a two-dimensional electronic image of the container sidewall that includes both of the container sidewall portions, and
   (b2) detecting commercial variations in the container sidewall as a function of such two-dimensional electronic image.

\* \* \* \* \*